(12) United States Patent
Nakashiro et al.

(10) Patent No.: US 8,889,649 B2
(45) Date of Patent: Nov. 18, 2014

(54) COMPOSITION CONTAINING ANTISENSE OLIGONUCLEOTIDE TO MICRO RNA

(75) Inventors: Koichi Nakashiro, Ehime (JP); Hiroyuki Hamakawa, Ehime (JP); Hiroshi Tanaka, Ehime (JP)

(73) Assignee: National University Corporation Ehime University, Ehime (JP)

( * ) Notice: Subject to any disclaimer, the term of this patent is extended or adjusted under 35 U.S.C. 154(b) by 0 days.

(21) Appl. No.: 13/884,436

(22) PCT Filed: Nov. 10, 2011

(86) PCT No.: PCT/JP2011/075924
§ 371 (c)(1),
(2), (4) Date: Oct. 31, 2013

(87) PCT Pub. No.: WO2012/063894
PCT Pub. Date: May 18, 2012

(65) Prior Publication Data
US 2014/0045917 A1  Feb. 13, 2014

(30) Foreign Application Priority Data
Nov. 12, 2010  (JP) ................................ 2010-254021

(51) Int. Cl.
*C12N 15/11*     (2006.01)
*C12Q 1/68*      (2006.01)
*A61K 31/7088*   (2006.01)
*C12N 15/113*    (2010.01)
*A61K 48/00*     (2006.01)

(52) U.S. Cl.
CPC .......... *C12N 15/113* (2013.01); *A61K 31/7088* (2013.01); *C12N 2310/3231* (2013.01); *A61K 48/00* (2013.01); *C12N 2330/31* (2013.01); *C12N 2310/113* (2013.01)
USPC ....................................... 514/44 A; 435/6.14

(58) Field of Classification Search
CPC ... C12N 2310/14; C12Q 1/00; A61K 2123/00
See application file for complete search history.

(56) References Cited

U.S. PATENT DOCUMENTS

| 2007/0161004 A1 | 7/2007 | Brown et al. |
| 2008/0050744 A1 | 2/2008 | Brown et al. |

FOREIGN PATENT DOCUMENTS

| JP | 2008-519606 A | 6/2006 |
| JP | 2008-500837 A | 1/2008 |
| JP | 2008-289488 A | 12/2008 |
| JP | 2009-532392 A | 9/2009 |
| WO | 03/070918 A2 | 8/2003 |
| WO | 2007/112754 A2 | 10/2007 |
| WO | 2010/056737 A2 | 5/2010 |

OTHER PUBLICATIONS

Schickel et al., "MicroRNAs: key players in the immune system, differentiation, tumorigenesis and cell death," Oncogene, 27: 5959-5974 (2008).
Weber et al., "A Limited Set of Human MicroRNA Is Deregulated in Follicular Thyroid Carcinoma," Journal of Clinical Endocrinology & Metabolism, 91: 3584-3591 (2006).
Search Report issued in corresponding International Patent Application No. PCT/JP2011/075924 dated Dec. 13, 2011.

*Primary Examiner* — Tracy Vivlemore
*Assistant Examiner* — Kate Poliakova
(74) *Attorney, Agent, or Firm* — Morgan, Lewis & Bockius LLP

(57) ABSTRACT

Provided is a composition that contains an antisense oligonucleotide to a micro RNA and is capable of inhibiting the growth of cancer cells. The present invention, as one aspect, relates to a composition for suppressing the growth of human cancer cells, the composition containing an antisense oligonucleotide to a micro RNA, wherein the micro RNA is selected from the group consisting of hsa-miR-133a, hsa-miR-133b, hsa-miR-346 and hsa-miR-361-3p. The present invention, as another aspect, relates to a composition for suppressing the growth of human head/neck cancer cells, the composition containing an antisense oligonucleotide to a micro RNA, wherein the micro RNA is selected from the group consisting of hsa-miR-92a, hsa-miR-133a, hsa-miR-133b, hsa-miR-139-5p, hsa-miR-197, hsa-miR-328, hsa-miR-346, hsa-miR-361-3p, hsa-miR-605, hsa-miR-766, hsa-miR-1228, hsa-miR-1252, hsa-miR-1260 and hsa-miR-1271.

13 Claims, 4 Drawing Sheets

COMPOSITION CONTAINING ANTISENSE OLIGONUCLEOTIDE TO MICRO RNA

TECHNICAL FIELD

The present invention relates to a composition containing an antisense oligonucleotide to a microRNA.

BACKGROUND ART

A microRNA (or miRNA) is a small molecule RNA composed of 18 to 25 bases, and binds to a target mRNA to inhibit the translation of the target mRNA into a protein. About 1100 types of human miRNAs have been registered in databases (e.g. miRBase (http://www.miRbase.org/)) so far, and it has been clarified that abnormalities in expression or functions of these miRNA are involved in various types of diseases (see Non-Patent Document 1). Particularly relating to cancers, many miRNAs whose expression is increased or suppressed in cancer tissues or cells have been identified by comprehensive expression analysis using miRNA microarrays (Patent Document 1).

As miRNAs whose expression increases in cancers, miR-21, miR-155, miR-17-5p, miR-19, and the like have been known. Among these, miR-19 is necessary and sufficient for cell tumorigenesis, and one of its targets is proved to be the cancer suppressing gene PTEN. Such a miRNA that has a property like an oncogene against a tumor suppressor gene is called "OncomiR".

Further, in the cases of many miRNAs, expression thereof decreases in cancers. As such miRNAs, let-7, miR-15a, miR-34a, miR-143, miR-145 and the like have been reported. Regarding let-7 among these, it has been proved that in lung cancer the decrease of expression of let-7 and the prognosis correlate each other, and it has been known that the targets thereof include the oncogene Ras. A miRNA that functions like a tumor suppressor gene against an oncogene is called "tumor suppressor miR".

On the other hand, attempts have been made to inhibit miRNA involved in diseases, such as the OncomiR, as the target molecule. For example, the following has been proposed: by introducing an antisense oligonucleotide having a sequence complementary to a target miRNA into cells, a double strand is formed with a target miRNA in each cell so that the function of the target miRNA is inhibited (Patent Document 2).

PRIOR ART DOCUMENT

Patent Document

Patent Document 1: JP2008-500837A
Patent Document 2: JP2009-532392A

Non-Patent Document

Non-Patent Document 1: Schickel R, et al. Oncogene 27: 5959-5974, 2008.

SUMMARY OF INVENTION

Problem to be Solved by the Invention

The identification of more OncomiRs and the development of molecules that are capable of inhibiting the OncomiRs are desired, in order to increase the potential of cancer treatment. The present invention provides a composition containing an antisense oligonucleotide to a microRNA, the composition being capable of inhibiting growth of cancer cells.

Means to Solve the Problem

The present invention, as one aspect, relates to a composition for suppressing growth of human cancer cells, the composition containing an antisense oligonucleotide to a microRNA, wherein the microRNA is selected from the group consisting of hsa-miR-133a, hsa-miR-133b, hsa-miR-346, and hsa-miR-361-3p.

The present invention, as another aspect, relates to a composition for suppressing growth of human head/neck cancer cells, the composition containing an antisense oligonucleotide to a microRNA, wherein the microRNA is selected from the group consisting of hsa-miR-92a, hsa-miR-133a, hsa-miR-133b, hsa-miR-139-5p, hsa-miR-197, hsa-miR-328, hsa-miR-346, hsa-miR-361-3p, hsa-miR-605, hsa-miR-766, hsa-miR-1228, hsa-miR-1252, hsa-miR-1260, and hsa-miR-1271.

Effect of the Invention

The present invention makes it possible to inhibit growth of cancer cells. Therefore, the present invention can contribute to the treatment and prevention of a cancer, and the prevention of recurrence of a cancer.

DESCRIPTION OF THE INVENTION

Figure 1:
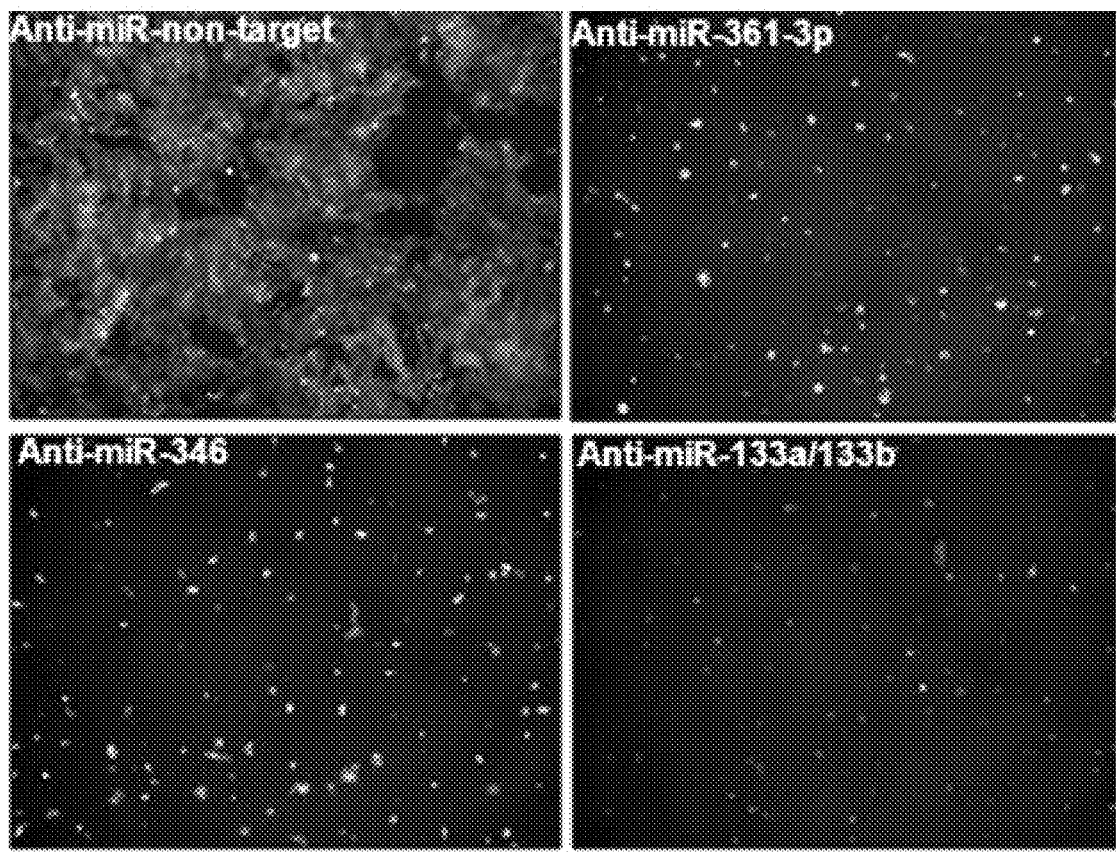
FIG. 1 is an exemplary fluorography showing influences of antisense oligonucleotides to microRNAs with respect to proliferation of human oral squamous cell cancer cells GFP-SAS.

The present invention relates to the following aspects:

[1] A composition for suppressing growth of human cancer cells, the composition containing an antisense oligonucleotide to a microRNA, wherein the microRNA is selected from the group consisting of hsa-miR-133a, hsa-miR-133b, hsa-miR-346, and hsa-miR-361-3p;

[2] A pharmaceutical composition for treatment or prevention of a human cancer, the pharmaceutical composition containing an antisense oligonucleotide to a microRNA, wherein the microRNA is selected from the group consisting of hsa-miR-133a, hsa-miR-133b, hsa-miR-346, and hsa-miR-361-3p;

[3] A composition for suppressing growth of non-human cancer cells, the composition containing an antisense oligonucleotide to a microRNA, wherein the microRNA is selected from the group consisting of miR-133, miR-346, and miR-361;

[4] The composition according to any one of [1] to [3], wherein the cancer is selected from the group consisting of head/neck cancer, lung cancer, biliary tract cancer, pancreas cancer, and prostate cancer;

[5] A composition for suppressing growth of human head/neck cancer cells, the composition containing an antisense oligonucleotide to a microRNA, wherein the microRNA is selected from the group consisting of hsa-miR-92a, hsa-miR-133a, hsa-miR-133b, hsa-miR-139-5p, hsa-miR-197, hsa-miR-328, hsa-miR-346, hsa-miR-361-3p, hsa-miR-605, hsa-miR-766, hsa-miR-1228, hsa-miR-1252, hsa-miR-1260, and hsa-miR-1271;

[6] A pharmaceutical composition for treatment or prevention of a human head/neck cancer, the pharmaceutical composition containing an antisense oligonucleotide to a microRNA, wherein the microRNA is selected from the group consisting of hsa-miR-92a, hsa-miR-133a, hsa-miR-133b, hsa-miR-139-5p, hsa-miR-197, hsa-miR-328, hsa-miR-346, hsa-miR-361-3p, hsa-miR-605, hsa-miR-766, hsa-miR-1228, hsa-miR-1252, hsa-miR-1260, and hsa-miR-1271;

[7] A composition for suppressing growth of non-human cancer cells, the composition containing an antisense oligonucleotide to a microRNA, wherein the microRNA is selected from the group consisting of miR-92, miR-133, miR-139, miR-197, miR-328, miR-346, miR-361, miR-605, miR-766, miR-1228, miR-1252, miR-1260, and miR-1271;

[8] A method for suppressing growth of human cancer cells, the method including: bringing a composition containing an antisense oligonucleotide to a microRNA into contact with the cancer cells, wherein the microRNA is selected from the group consisting of hsa-miR-133a, hsa-miR-133b, hsa-miR-346, and hsa-miR-361-3p;

[9] A method for treating or preventing a human cancer, the method including: administering a composition containing an antisense oligonucleotide to a microRNA to an object, wherein the microRNA is selected from the group consisting of hsa-miR-133a, hsa-miR-133b, hsa-miR-346, and hsa-miR-361-3p;

[10] A method for suppressing growth of non-human cancer cells, the method including: bringing a composition containing an antisense oligonucleotide to a microRNA into contact with the cancer cells, wherein the microRNA is selected from the group consisting of miR-133, miR-346, and miR-361;

[11] The method according to any one of [8] to [10], wherein the cancer is selected from the group consisting of head/neck cancer, lung cancer, biliary tract cancer, pancreas cancer, and prostate cancer;

[12] A method for suppressing growth of human head/neck cancer cells, the method including: bringing a composition containing an antisense oligonucleotide to a microRNA into contact with the cancer cells, wherein the microRNA is selected from the group consisting of hsa-miR-92a, hsa-miR-133a, hsa-miR-133b, hsa-miR-139-5p, hsa-miR-197, hsa-miR-328, hsa-miR-346, hsa-miR-361-3p, hsa-miR-605, hsa-miR-766, hsa-miR-1228, hsa-miR-1252, hsa-miR-1260, and hsa-miR-1271;

[13] A method for treating or preventing human head/neck cancer, the method including: administering a composition to an object, the composition containing an antisense oligonucleotide to a microRNA, wherein the microRNA is selected from the group consisting of hsa-miR-92a, hsa-miR-133a, hsa-miR-133b, hsa-miR-139-5p, hsa-miR-197, hsa-miR-328, hsa-miR-346, hsa-miR-361-3p, hsa-miR-605, hsa-miR-766, hsa-miR-1228, hsa-miR-1252, hsa-miR-1260, and hsa-miR-1271; and

[14] A method for suppressing growth of non-human head/neck cancer cells, the method including: bringing a composition into contact with the cancer cells, the composition containing an antisense oligonucleotide to a microRNA, wherein the microRNA is selected from the group consisting of miR-92, miR-133, miR-139, miR-197, miR-328, miR-346, miR-361, miR-605, miR-766, miR-1228, miR-1252, miR-1260, and miR-1271.

In the present specification, a "microRNA (or miRNA)" refers to one type of a low-molecular non-coding RNA, which is a usual meaning thereof used in the art. Any microRNA referred to by using its ID in the present specification can be referred to in a database (e.g., miRBase (http://www.miRbase.org/)). A microRNA in the present specification refers to a mature microRNA composed of 18 to 25 bases, unless otherwise provided.

In the present specification, an "antisense oligonucleotide to a microRNA" refers to an oligonucleotide having a base sequence complementary to a microRNA as a target, and is preferably in the form of a single-strand oligonucleotide. As one embodiment of the present invention, the antisense oligonucleotide to a microRNA is an oligonucleotide that includes a base sequence complementary to an entirety or a part of a base sequence of a mature microRNA as a target, and is more preferably an oligonucleotide that includes a base sequence complementary to an entirety or a part of a base sequence of a mature microRNA as a target.

An "oligonucleotide to a microRNA" in the present invention has a length of, for example, 8 to 25 nucleotides, 10 to 24 nucleotides, 10 to 22 nucleotides, 12 to 22 nucleotides, 10 to 20 nucleotides, 12 to 20 nucleotides, 10 to 19 nucleotides, 12 to 19 nucleotides, 10 to 18 nucleotides, 12 to 18 nucleotides, 10 to 17 nucleotides, 12 to 17 nucleotides, 10 to 16 nucleotides, or 12 to 16 nucleotides, in one embodiment. It is expected that the non-specific microRNA inhibition can be further suppressed by decreasing the length of the sequence of the oligonucleotide.

In the present specification, "complementary (or complementation)" refers to a phenomenon that two nucleotide sequences are capable of forming a pair correctly with each other. For example, if a certain oligonucleotide, at a certain position, can form a hydrogen bond with a nucleotide at a corresponding position in a microRNA as a target, it can be considered that the oligonucleotide and the microRNA are complementary to each other at the position. When a sufficient number of nucleotides in the oligonucleotide can form hydrogen bonds with corresponding nucleotides in the target microRNA and thereby form a stable complex, it can be considered that the oligonucleotide and the microRNA are complementary to each other. In order for a sequence of an oligonucleotide to be stable in vitro or in vivo, it is not necessary that the sequence of the oligonucleotide is completely (100%) complementary to its target micro RNA. In other words, the term "complementary" and the phrase "specifically hybridized" mean that an oligonucleotide sufficiently strongly and specifically bond to a target molecule, and provides desirable interference with target normal functions without giving influences to functions of non-target microRNAs. In another embodiment of the present invention, an antisense oligonucleotide to a microRNA preferably includes, or is composed of, a base sequence completely (100%) complementary to a microRNA as a target.

In the present specification, a pair of nucleotides refers to a hydrogen bond between bases; in terms of DNAs, it refers to a bond between A and T or a bond between G and C; and in terms of RNAs, examples of the same include a bond between A and U and a bond between G and C. An antisense oligonucleotide to a microRNA may be an analog other than the above-described A, T (U), G, and C as long as it can be paired with a nucleotide of a microRNA as a target.

In the present specification, an "oligonucleotide" refers to DNAs and RNAs, as well as known nucleic acid analogs, and oligonucleotides formed by mixing these. Examples of the above-described oligonucleotide include modified oligonucleotides that are obtained by known modifications. Examples of the nucleic acid analog include known nucleic acid analogs such as LNAs (locked nucleic acids) and PNAs (peptide nucleic acids). From the viewpoint of improving the specificity to a target microRNA and improving the cell proliferation inhibition, an antisense oligonucleotide referred to in the present specification preferably contains a nucleic acid analog, more preferably contains a LNA, and further preferably contains more than 50% of a nucleic acid analog. As to the microRNA-antisense oligonucleotide containing a LNA, refer to, for example, JP2009-532392A (WO2007/00169).

In the present specification, a base in an "antisense oligonucleotide to a microRNA" may be a non-DNA/RNA base other than the bases of DNAs and RNAs as long as the base can inhibit functions of a target microRNA, and the antisense oligonucleotide may be in the form of a DNA or a RNA including a fluorine substituent or the like. In the "antisense oligonucleotide to a microRNA" referred to in the present specification, the bond between nucleosides may be a bond other than a phosphoester bond, and is preferably a bond containing sulfur (S) (that is, the nucleotide is a phosphorothioate oligonucleotide), from the viewpoint of stability. It should be noted that a known or commercially-available antisense oligonucleotide to a microRNA can be used as the "antisense oligonucleotide to a microRNA" referred to in the present specification.

In the present specification, the "suppression of cell growth" encompasses the inhibition of cell proliferation and the death of cells, as well as the suppression of cell growth in vivo, in vitro, and ex vivo. In the present specification, the "cell" encompasses a human cell and a non-human cell. Examples of the non-human cell include those of organisms that have the microRNA mechanism. Further, in the present specification, "non-human" encompasses primates other than humans, mammals other than humans, and vertebrates other than humans.

[First Composition]

The present invention, as one aspect, relates to a composition for suppressing growth of human cancer cells, the composition containing an antisense oligonucleotide to a microRNA, wherein the microRNA is selected from the group consisting of hsa-miR-133a, hsa-miR-133b, hsa-miR-346, and hsa-miR-361-3p (hereinafter this composition is referred to as the "first composition of the present invention" as well). The sequences of these microRNAs (mature) are shown in SEQ ID NOS. 1 to 4 in Table 1 below.

Examples of the antisense oligonucleotide to a microRNA that can be contained in the first composition of the present invention include oligonucleotides each of which is composed of any one of base sequences of SEQ ID NOS. 5 to 8 in Table 1 above or partial sequences of the same. The length and the nucleic acid analog of the oligonucleotide are as described above. It should be noted that the first composition of the present invention may contain one type or a plurality of types of antisense oligonucleotides.

It should be noted that in the present specification, one embodiment of the antisense oligonucleotide to the microRNA of hsa-miR-133a or hsa-miR-133b encompasses an antisense oligonucleotide that is capable of inhibiting both of hsa-miR-133a and hsa-miR-133b.

Cancers of human cancer cells, growth of which is to be suppressed by the first composition of the present invention, are not limited particularly, and examples of the same include head/neck cancer, melanocarcinoma, basal cell cancer, ovary cancer, breast cancer, non-small cell lung cancer, renal cell cancer, bladder cancer, recurrent superficial bladder cancer, stomach cancer, prostate cancer, biliary tract cancer, pancreas cancer, lung cancer, uterine cervix cancer, cervical dysplasia, laryngeal papillomatosis, colon cancer, colorectal cancer, and carcinoid tumor. Cancers of human cancer cells, growth of which is to be suppressed by the composition of the present aspect, preferably encompass head/neck cancer, lung cancer, biliary tract cancer, pancreas cancer, and prostate cancer.

In the present specification, "head/neck cancer" refers to a cancer that occurs at and above the neck except for the brain and the eyes, and generally encompasses oral cancer, nose/paranasal sinus cancer, lip cancer, pharynx cancer, larynx cancer, neck tumor, and ear cancer. In the present specification, the oral cancer generally encompasses cancers that occur at mucous membranes of parts that compose the oral cavity, such as the gum, the tongue, the buccal region, the palate, the mouth floor, and the salivary gland.

The first composition of the present invention may contain a reagent, a medical agent, and a medium that are suitable for being brought into contact with target human cancer cells and suppressing the growth of the cells. The first composition of the present invention may be in a freeze-dried form.

[First Pharmaceutical Composition]

The first composition of the present invention described above can be used as a pharmaceutical composition for treatment or prevention of the above-described cancers. Therefore, the present invention, as another aspect, relates to a pharmaceutical composition for treatment or prevention of a human cancer, the pharmaceutical composition containing an antisense oligonucleotide to a microRNA, wherein the microRNA is selected from the group consisting of hsa-

TABLE 1

| DataBase ID | Accession No. | Sequence (5'→3') | Seq ID | Complement Sequence (5'→3') | Seq ID |
|---|---|---|---|---|---|
| hsa-miR-133a/b | MIMAT0000427 | UUUGGUCCCCUUCAACCAGCUG | 1 | CAGCTGGTTGAAGGGGACCAAA | 5 |
|  | MIMAT0000770 | UUUGGUCCCCUUCAACCAGCUA | 2 | TAGCTGGTTGAAGGGGACCAAA | 6 |
| hsa-miR-346 | MIMAT0000773 | UGUCUGCCCGCAUGCCUGCCUCU | 3 | AGAGGCAGGCATGCGGGCAGACA | 7 |
| hsa-miR-361-3p | MIMAT0004682 | UCCCCCAGGUGUGAUUCUGAUUU | 4 | AAATCAGAATCACACCTGGGGGA | 8 | miR133a, hsa-miR-133b, hsa-miR-346, and hsa-miR-361-3p (hereinafter the pharmaceutical composition is referred to as "the first pharmaceutical composition of the present invention" as well). In the present specification, the prevention of a cancer encompasses the prevention of recurrence of a cancer.

Examples of the antisense oligonucleotide to a microRNA that can be contained in the first pharmaceutical composition of the present invention include oligonucleotides each of which is composed of any one of base sequences of SEQ ID NOS. 5 to 8 in Table 1 above or partial sequences of the same. The length and the nucleic acid analog of the oligonucleotide are as described above. It should be noted that the first pharmaceutical composition of the present invention may contain one type or a plurality of types of antisense oligonucleotides.

The first pharmaceutical composition of the present invention may further contain a carrier that is pharmaceutically allowed. The pharmaceutical carrier above is not limited particularly, and examples of the same include carriers that can allow the antisense oligonucleotide to a microRNA to more efficiently invade into a target site, tissue, cell, or the like; for example, atelocollagen, liposome, and cationic liposome. The dosage form of the pharmaceutical composition of the present aspect is not limited particularly, and may be, for example, an injection form, a cream form, an ointment form, a pill form, a suspension form, or the like. The administration method for the same is not limited particularly, either, and the pharmaceutical composition may be administered, for example, by injection, orally, topically, intranasally, rectally, intravenously, intra-arterially, or the like.

[Second Composition]

The present invention, as still another aspect, relates to a composition for suppressing growth of non-human cancer cells, the composition containing an antisense oligonucleotide to a microRNA, wherein the microRNA is selected from the group consisting of miR-133, miR-346, and miR-361 (hereinafter this composition is referred to as the "second composition of the present invention" as well). For example, in the case where the growth of cancer cells of dogs is to be suppressed, an antisense nucleotide to a microRNA selected from the group consisting of cfa-miR-133a/b/c (MIMIAT0009834, 0009835, 0009833), cfa-miR-346 (MIMIAT0004949), and cfa-miR-361 (MIMIAT0006751) can be used. With respect to other organisms as well, antisense nucleotides to corresponding microRNA sequences can be used. It should be noted that the second composition of the present invention may contain one type or a plurality of types of antisense oligonucleotides.

Cancers of non-human cancer cells, growth of which is to be suppressed by the second composition of the present invention, are not limited particularly, and examples of the cancer include head/neck cancer, melanocarcinoma, basal cell cancer, ovary cancer, breast cancer, non-small cell lung cancer, renal cell cancer, bladder cancer, recurrent superficial bladder cancer, stomach cancer, prostate cancer, biliary tract cancer, pancreas cancer, lung cancer, uterine cervix cancer, cervical dysplasia, laryngeal papillomatosis, colon cancer, colorectal cancer, and carcinoid tumor. Cancers of non-human cancer cells, growth of which is to be suppressed by the composition of the present aspect, preferably encompass head/neck cancer, lung cancer, biliary tract cancer, pancreas cancer, and prostate cancer. The second composition of the present invention may contain a reagent, a medical agent, and a medium that are suitable for being brought into contact with target non-human cancer cells and suppressing the growth of the cells. The second composition of the present invention may be in a freeze-dried form.

[Second Pharmaceutical Composition]

The second composition of the present invention described above can be used as a pharmaceutical composition for treatment or prevention of the above-described cancers. Therefore, the present invention, as still another aspect, relates to a pharmaceutical composition for treatment or prevention of a non-human cancer, the pharmaceutical composition containing an antisense oligonucleotide to a microRNA, wherein the microRNA is selected from the group consisting of hsa-miR133a, hsa-miR-133b, hsa-miR-346, and hsa-miR-361-3p (hereinafter the pharmaceutical composition is referred to as "the second pharmaceutical composition of the present invention" as well). The length and the nucleic acid analog of the antisense oligonucleotide to the microRNA that can be contained in the second pharmaceutical composition of the present invention are as described above. It should be noted that the second pharmaceutical composition of the present invention may contain one type or a plurality of types of antisense oligonucleotides.

The second pharmaceutical composition of the present invention may further contain a carrier that is pharmaceutically allowed. The pharmaceutical carrier is not limited particularly, and examples of the same include carriers that can allow the antisense oligonucleotide to a microRNA to more efficiently invade into a target site, tissue, cell, or the like; for example, atelocollagen, liposome, and cationic liposome. The dosage form of the pharmaceutical composition of the present aspect is not limited particularly, and may be, for example, an injection form, a cream form, an ointment form, a pill form, a suspension form, or the like. The administration method for the same is not limited particularly, either, and the pharmaceutical composition may be administered, for example, by injection, orally, topically, intranasally, rectally, intravenously, intra-arterially, or the like.

[Third Composition]

The present invention, as still another aspect, relates to a composition for suppressing growth of human head/neck cancer cells, the composition containing an antisense oligonucleotide to a microRNA, wherein the microRNA is selected from the group consisting of hsa-miR-92a, hsa-miR-133a, hsa-miR-133b, hsa-miR-139-5p, hsa-miR-197, hsa-miR-328, hsa-miR-346, hsa-miR-361-3p, hsa-miR-605, hsa-miR-766, hsa-miR-1228, hsa-miR-1252, hsa-miR-1260, and hsa-miR-1271 (hereinafter this composition is referred to as the "third composition of the present invention" as well). It should be noted that the third composition of the present invention may contain one type or a plurality of types of antisense oligonucleotides.

The third composition of the present invention, in one embodiment, is intended to suppress the growth of human oral squamous cell cancer, and contains an antisense nucleotide to a microRNA as a target, wherein the microRNA is selected from the group consisting of hsa-miR-92a, hsa-miR-133a, hsa-miR-133b, hsa-miR-139-5p, hsa-miR-197, hsa-miR-328, hsa-miR-346, hsa-miR-361-3p, hsa-miR-605, hsa-miR-766, hsa-miR-1228, hsa-miR-1252, hsa-miR-1260, and hsa-miR-1271. The sequences of the microRNAs (mature) as targets are preferably those of SEQ ID NOS. 1 to 4 and 9 to 18 shown in Table 2 below. Examples of the antisense oligonucleotide to a microRNA, which can be contained in the third composition of the present embodiment, include oligonucleotides each of which is composed of any one of base sequences of SEQ ID NOS. 5 to 8 and 19 to 28 in Table 2 below or partial sequences of the same. The length and the nucleic acid analog of the oligonucleotide are as described above.

TABLE 2

| DataBase ID | Accession No. | Sequence (5'→3') | Complement Seq ID | Sequence (5'→3') | Seq ID |
|---|---|---|---|---|---|
| hsa-miR-92a | MIMAT0000092 | UAUUGCACUUGUCCCGGCCUGU | 9 | ACAGGCCGGGACAAGTGCAATA | 19 |
| hsa-miR-133a/b | MIMAT0000427 | UUUGGUCCCCUUCAACCAGCUG | 1 | CAGCTGGTTGAAGGGGACCAAA | 5 |
|  | MIMAT0000770 | UUUGGUCCCCUUCAACCAGCUA | 2 | TAGCTGGTTGAAGGGGACCAAA | 6 |
| hsa-miR-139-5p | MIMAT0000250 | UCUACAGUGCACGUGUCUCCAG | 10 | CTGGAGACACGTGCACTGTAGA | 20 |
| hsa-miR-197 | MIMAT0000227 | UUCACCACCUUCUCCACCCAGC | 11 | GCTGGGTGGAGAAGGTGGTGAA | 21 |
| hsa-miR-328 | MIMAT0000752 | CUGGCCCUCUCUGCCCUUCCGU | 12 | ACGGAAGGGCAGAGAGGGCCAG | 22 |
| hsa-miR-346 | MIMAT0000773 | UGUCUGCCCGCAUGCCUGCCUCU | 3 | AGAGGCAGGCATGCGGGCAGACA | 7 |
| hsa-miR-361-3p | MIMAT0004682 | UCCCCCAGGUGUGAUUCUGAUUU | 4 | AAATCAGAATCACACCTGGGGGA | 8 |
| hsa-miR-605 | MIMAT0003273 | UAAAUCCCAUGGUGCCUUCUCCU | 13 | AGGAGAAGGCACCATGGGATTTA | 23 |
| hsa-miR-766 | MIMAT0003888 | ACUCCAGCCCCACAGCCUCAGC | 14 | GCTGAGGCTGTGGGCTGGAGT | 24 |
| hsa-miR-1228 | MIMAT0005583 | UCACACCUGCCUCGCCCCCC | 15 | GGGGGGCGAGGCAGGTGTGA | 25 |
| hsa-miR-1252 | MIMAT0005944 | AGAAGGAAAUUGAAUUCAUUUA | 16 | TAAATGAATTCAATTTCCTTCT | 26 |
| hsa-miR-1260 | MIMAT0005911 | AUCCCACCUCUGCCACCA | 17 | TGGTGGCAGAGGTGGGAT | 27 |
| hsa-miR-1271 | MIMAT0005796 | CUUGGCACCUAGCAAGCACUCA | 18 | TGAGTGCTTGCTAGGTGCCAAG | 28 |

The third composition of the present invention, in another embodiment, is intended to suppress the growth of human salivary gland cancer, and contains an antisense nucleotide to a microRNA as a target, wherein the microRNA is selected from the group consisting of hsa-miR-133a, hsa-miR-133b, and hsa-miR-361-3p. The sequences of the microRNAs (mature) as targets are preferably those of SEQ ID NOS. 1, 2, and 4 shown in Table 3 below. Examples of the antisense oligonucleotide to a microRNA, which can be contained in the third composition of the present embodiment, include oligonucleotides each of which is composed of any one of base sequences of SEQ ID NOS. 5, 6, and 8 in Table 3 below or partial sequences of the same. The length and the nucleic acid analog of the oligonucleotide are as described above.

The third composition of the present invention may contain a reagent, a medical agent, and a medium that are suitable for being brought into contact with target human cancer cells and suppressing the growth of the cells. The third composition of the present invention may be in a freeze-dried form.

[Third Pharmaceutical Composition]

The third composition of the present invention described above can be used as a pharmaceutical composition for treatment or prevention of human head/neck cancers. Therefore, the present invention, as still another aspect, relates to a pharmaceutical composition for treatment or prevention of a human head/neck cancer, the pharmaceutical composition containing an antisense oligonucleotide to a microRNA, wherein the microRNA is selected from the group consisting

TABLE 3

| DataBase ID | Accession No. | Sequence (5'→3') | Complement Seq ID | Sequence (5'→3') | Seq ID |
|---|---|---|---|---|---|
| hsa-miR-133a/b | MIMAT0000427 | UUUGGUCCCCUUCAACCAGCUG | 1 | CAGCTGGTTGAAGGGGACCAAA | 5 |
|  | MIMAT0000770 | UUUGGUCCCCUUCAACCAGCUA | 2 | TAGCTGGTTGAAGGGGACCAAA | 6 |
| hsa-miR-361-3p | MIMAT0004682 | UCCCCCAGGUGUGAUUCUGAUUU | 4 | AAATCAGAATCACACCTGGGGGA | 8 | of hsa-miR-92a, hsa-miR-133a, hsa-miR-133b, hsa-miR-139-5p, hsa-miR-197, hsa-miR-328, hsa-miR-346, hsa-miR-361-3p, hsa-miR-605, hsa-miR-766, hsa-miR-1228, hsa-miR-1252, hsa-miR-1260, and hsa-miR-1271 (hereinafter the pharmaceutical composition is referred to as "the third pharmaceutical composition of the present invention" as well). It should be noted that the third pharmaceutical composition of the present invention may contain one type or a plurality of types of antisense oligonucleotides.

The third pharmaceutical composition of the present invention, in one embodiment, is intended to be used for treatment or prevention of a human oral squamous cell cancer, and contains an antisense nucleotide to a microRNA as a target, wherein the microRNA is selected from the group consisting of hsa-miR-92a, hsa-miR-133a, hsa-miR-133b, hsa-miR-139-5p, hsa-miR-197, hsa-miR-328, hsa-miR-346, hsa-miR-361-3p, hsa-miR-605, hsa-miR-766, hsa-miR-1228, hsa-miR-1252, hsa-miR-1260, and hsa-miR-1271. The sequences of the microRNAs (mature) as a target are preferably those of SEQ ID NOS. 1 to 4 and 9 to 18 shown in Table 2 above. Examples of the antisense oligonucleotide to a microRNA, which can be contained in the third pharmaceutical composition of the present embodiment, include oligonucleotides each of which is composed of any one of base sequences of SEQ ID NOS. 5 to 8 and 19 to 28 in Table 2 above or partial sequences of the same. The length and the nucleic acid analog of the oligonucleotide are as described above.

The third pharmaceutical composition of the present invention, in another embodiment, is intended be used for treatment or prevention of human salivary gland cancer, and contains an antisense nucleotide to a microRNA as a target, wherein the microRNA is selected from the group consisting of hsa-miR-133a, hsa-miR-133b, and hsa-miR-361-3p. The sequences of the microRNAs (mature) as targets are preferably those of SEQ ID NOS. 1, 2, and 4 shown in Table 3 above. Examples of the antisense oligonucleotide to a microRNA, which can be contained in the third pharmaceutical composition of the present embodiment, include oligonucleotides each of which is composed of any one of base sequences of SEQ ID NOS. 5, 6, and 8 in Table 3 above or partial sequences of the same. The length and the nucleic acid analog of the oligonucleotide are as described above.

The third pharmaceutical composition of the present invention may contain a carrier that is pharmaceutically allowed. The pharmaceutical carrier is not limited particularly, and examples of the same include carriers that can allow the antisense oligonucleotide to a microRNA to more efficiently invade into a target site, tissue, cell, or the like; for example, atelocollagen, liposome, and cationic liposome. The dosage form of the pharmaceutical composition of the present aspect is not limited particularly, and may be, for example, an injection form, a cream form, an ointment form, a pill form, a suspension form, or the like. The administration method for the same is not limited particularly, either, and the pharmaceutical composition may be administered, for example, by injection, orally, topically, intranasally, rectally, intravenously, intra-arterially, or the like.

[Fourth Composition]

The present invention, as still another aspect, relates to a composition for suppressing growth of non-human cancer cells, the composition containing an antisense oligonucleotide to a microRNA, wherein the microRNA is selected from the group consisting of miR-92, miR-133, miR-139, miR-197, miR-328, miR-346, miR-361, miR-605, miR-766, miR-1228, miR-1252, miR-1260, and miR-1271 (hereinafter this composition is referred to as the "fourth composition of the present invention" as well). It should be noted that the fourth composition of the present invention may contain one type or a plurality of types of antisense oligonucleotides. The length and the nucleic acid analog of the oligonucleotide that can be contained are as described above. It should be noted that the fourth composition of the present invention may be in a freeze-dried form.

The fourth composition of the present invention, in one embodiment, is intended to suppress the growth of non-human oral squamous cell cancer, and contains an antisense nucleotide to a microRNA as a target, wherein the microRNA is selected from the group consisting of miR-92, miR-133, miR-139, miR-197, miR-328, miR-346, miR-361, miR-605, miR-766, miR-1228, miR-1252, miR-1260, and miR-1271. With regard to the sequences of the antisense nucleotides, corresponding microRNA sequences in non-human organisms as intended objects can be used.

The fourth composition of the present invention, in another embodiment, is intended to suppress the growth of non-human salivary gland cancer, and contains an antisense nucleotide to a microRNA as a target, wherein the microRNA is selected from the group consisting of miR-133a, miR-133b, and miR-361-3p. With regard to the sequences of the antisense nucleotides, corresponding microRNA sequences in non-human organisms as intended objects can be used.

[Fourth Pharmaceutical Composition]

The fourth composition of the present invention described above can be used as a pharmaceutical composition for treatment or prevention of a non-human head/neck cancer. Therefore, the present invention, as still another aspect, relates to a pharmaceutical composition for treatment or prevention of a non-human head/neck cancer, the pharmaceutical composition being a pharmaceutical composition for non-human use containing an antisense oligonucleotide to a microRNA, wherein the microRNA is selected from the group consisting of miR-92, miR-133, miR-139, miR-197, miR-328, miR-346, miR-361, miR-605, miR-766, miR-1228, miR-1252, miR-1260, and miR-1271 (hereinafter the pharmaceutical composition is referred to as "the fourth pharmaceutical composition of the present invention" as well). The length and the nucleic acid analog of the antisense oligonucleotide to a microRNA, which can be contained in the fourth pharmaceutical composition of the present invention, are as described above. It should be noted that the fourth pharmaceutical composition of the present invention may contain one type or a plurality of types of antisense oligonucleotides.

The fourth pharmaceutical composition of the present invention, in one embodiment, is intended be used for treatment or prevention of non-human oral squamous cell cancer, and contains an antisense nucleotide to a microRNA as a target, wherein the microRNA is selected from the group consisting of miR-92, miR-133, miR-139, miR-197, miR-328, miR-346, miR-361, miR-605, miR-766, miR-1228, miR-1252, miR-1260, and miR-1271. With regard to the sequences of the antisense nucleotides, corresponding microRNA sequences in non-human organisms as intended objects can be used.

The fourth pharmaceutical composition of the present invention, in another embodiment, is intended be used for treatment or prevention of non-human salivary gland cancer, and contains an antisense nucleotide to a microRNA as a target, wherein the microRNA is selected from the group consisting of miR-133a, miR-133b, and miR-361-3p. With regard to the sequences of the antisense nucleotides, corresponding microRNA sequences in non-human organisms as intended objects can be used.

The fourth pharmaceutical composition of the present invention may further contain a carrier that is pharmaceutically allowed. The pharmaceutical carrier is not limited particularly, and examples of the same include carriers that can allow the antisense oligonucleotide to a microRNA to more efficiently invade into a target site, tissue, cell, or the like; for example, atelocollagen, liposome, and cationic liposome. The dosage form of the pharmaceutical composition of the present aspect is not limited particularly, and may be, for example, an injection form, a cream form, an ointment form, a pill form, a suspension form, or the like. The administration method for the same is not limited particularly, either, and the pharmaceutical composition may be administered, for example, by injection, orally, topically, intranasally, rectally, intravenously, intra-arterially, or the like.

[Method for Human Cancer Cell Proliferation Inhibition]

With the first and third compositions of the present invention, the growth of human cancer cells as intended objects can be suppressed. Therefore, the present invention, as still another aspect, relates to a method for suppressing the growth of cancer cells, the method including bringing these compositions into contact with human cancer cells as intended objects. The method of contact is not limited particularly, and any method by which the antisense oligonucleotide to a microRNA in the above-described composition can be introduced into cancer cells as intended objects can be used. Lipofection is one of examples of embodiments for introducing an antisense oligonucleotide to a micro RNA to cancer cells. An amount of administration of the antisense oligonucleotide to cells upon introduction by lipofection or another method is, for example, 10 to 25 nM.

[Method for Treatment or Prevention of Human Cancers]

The first and third pharmaceutical compositions of the present invention enable the treatment or prevention of human cancers as intended objects. Therefore, the present invention, as still another aspect, relates to a method for suppressing the growth of cancer cells, the method including administering these compositions to an object. The dosage form of the composition to be administered is not limited particularly, and may be, for example, an injection form, a cream form, an ointment form, a pill form, a suspension form, or the like. The administration method for the same is not limited particularly, either, and the pharmaceutical composition may be administered, for example, by injection, orally, topically, intranasally, rectally, intravenously, intra-arterially, or the like. The administration depends on the severity and reactivity of a disease state to be treated, and the course of treatment. The optimal administration schedule can be calculated based on a measured accumulated amount of a medical agent in an object body. The optimal dose varies with relative effectiveness of each oligonucleotide. Generally, the optimal dose can be estimated based on EC50 as a value proved to be effective in in-vitro and in-vivo animal models. Generally, the dose is 0.01 µg to 1 g/kg body weight, preferably 0.01 to 100 mg/kg body weight, and more preferably 1 to 10 mg/kg body weight. As to the number of times of administration, the composition can be administered once a day, a week, a month or a year, or more than that; once a two to ten years; or continuously by injection for several hours to several months. The number of times of repeated administration can be estimated based on the concentration and the retention time of the medical agent in a body fluid or tissue subjected to the measurement. It is desirable in some cases that after the successful treatment, the object is subjected to maintenance therapy in order to prevent the recurrence of the disease.

[Method for Non-Human Cancer Cell Proliferation Inhibition]

With the second and fourth compositions of the present invention, the growth of non-human cancer cells as intended objects can be suppressed. Therefore, the present invention, as still another aspect, relates to a method for suppressing the growth of cancer cells, the method including bringing these compositions into contact with non-human cancer cells as intended objects. The method of contact is not limited particularly, and any method by which the antisense oligonucleotide to a microRNA in the above-described composition can be introduced into cancer cells as intended objects can be used.

[Method for Treatment or Prevention of Non-Human Cancers]

The second and fourth pharmaceutical compositions of the present invention enable the treatment or prevention of non-human cancers as intended objects. Therefore, the present invention, as still another aspect, relates to a method for suppressing the growth of cancer cells, the method including administering these compositions to a non-human object. The dosage form of the composition to be administered is not limited particularly, and may be, for example, an injection form, a cream form, an ointment form, a pill form, a suspension form, or the like. The administration method for the same is not limited particularly, either, and the pharmaceutical composition may be administered, for example, by injection, orally, topically, intranasally, rectally, intravenously, intra-arterially, or the like. The administration depends on the severity and reactivity of a disease state to be treated, and the course of treatment. The optimal administration schedule can be calculated based on a measured accumulated amount of a medical agent in an object body. The optimal dose can vary with relative effectiveness of each oligonucleotide. Generally, the optimal dose can be estimated based on EC50 as a value proved to be effective in in-vitro and in-vivo animal models. Generally, the dose is 0.01 µg to 1 g/kg body weight, preferably 0.01 to 100 mg/kg body weight, and more preferably 1 to 10 mg/kg body weight. As to the number of times of administration, the composition can be administered once a day, a week, a month or a year, or more than that; once a two to ten years; or continuously by injection for several hours to several months. The number of times of repeated administration can be estimated based on the concentration and the retention time of the medical agent in a body fluid or tissue subjected to the measurement. It is desirable in some cases that after the successful treatment, the object is subjected to maintenance therapy in order to prevent the recurrence of the disease.

EXAMPLE

1. Identification of OncomiR in Human Head/Neck Cancer Cells

Using a miRNA knockdown library, comprehensive analysis was carried out with respect to influences to growth of human head/neck cancer cell lines of the following two types in the case where microRNAs in the cell lines were inhibited. More specifically, the analysis was carried out under the following conditions.

[Cell Line Used]

Used were GFP stably expressing cell lines GFP-SAS and GFP-ACCM that were obtained by introducing green fluorescent protein (GFP) genes into human oral squamous cell cancer cell lines SAS and human salivary gland cancer cell lines ACCM, and separating and establishing the same.

[Comprehensive Function Analysis Using miRNA Knockdown Library]

The following were mixed and placed in each well of 96-well plastic plates (trade name: BD Falcon, manufactured by BD): 10% FBS-containing DMEM culture medium containing $2\times10^3$ human oral cancer cell lines GFP-SAS or GFP-ACCM, 160 μl each; LNA (locked nucleic acid)/DNA knockdown probe (trade name: miRCURY LNA™ microRNA Knockdown Library-Human v12.0, manufactured by EXIQON) with respect to 918 types of human microRNAs, 5 pmol each; and Opti-MEM (manufactured by Invitrogen) containing 0.4 μl of RNAiMAX (manufactured by Invitrogen), 40 μl each. After cultivation for 80 hours, a GFP fluorescence intensity of each well was measured by Wallac ARVO MX 1420 Multilabel Counter (manufactured by PerkinElmer), and subsequently the number of cells was counted using Cell Counting Kit-8 (manufactured by Dojindo)

By the above-described comprehensive function analysis using the knockdown library 14 types of OncomiRs were identified in the human oral squamous cell cancer cells GFP-SAS (Table 4 below), and 2 types of OncomiRs were identified in the human salivary gland cancer cells GFP-ACCM (Table 5 below). It should be noted that both of the two types of OncomiRs in the human salivary gland cancer cells were also OncomiRs in the human oral squamous cell cancer cells. It should be noted that Tables 4 and 5 show IDs, accession numbers, and sequences of mature microRNAs of the identified OncomiRs in miRBase (database).

TABLE 4

OncomiR that sustains the malignant phenotype of human oral squamous cell cancer cells

| ID | Accession No. | Sequence (5'→3') | Seq ID |
|---|---|---|---|
| hsa-miR-92a | MIMAT0000092 | UAUUGCACUUGUCCCGGCCUGU | 9 |
| hsa-miR-133a/b | MIMAT0000427 | UUUGGUCCCCUUCAACCAGCUG | 1 |
|  | MIMAT0000770 | UUUGGUCCCCUUCAACCAGCUA | 2 |
| hsa-miR-133b | MIMAT0000770 | UUUGGUCCCCUUCAACCAGCUA | 2 |
| hsa-miR-139-5p | MIMAT0000250 | UCUACAGUGCACGUGUCUCCAG | 10 |
| hsa-miR-197 | MIMAT0000227 | UUCACCACCUUCUCCACCCAGC | 11 |
| hsa-miR-328 | MIMAT0000752 | CUGGCCCUCUCUGCCCUUCCGU | 12 |
| hsa-miR-346 | MIMAT0000773 | UGUCUGCCCGCAUGCCUGCCUCU | 3 |
| hsa-miR-361-3p | MIMAT0004682 | UCCCCCAGGUGUGAUUCUGAUUU | 4 |
| hsa-miR-605 | MIMAT0003273 | UAAAUCCCAUGGUGCCUUCUCCU | 13 |
| hsa-miR-766 | MIMAT0003888 | ACUCCAGCCCCACAGCCUCAGC | 14 |
| hsa-miR-1228 | MIMAT0005583 | UCACACCUGCCUCGCCCCC | 15 |
| hsa-miR-1252 | MIMAT0005944 | AGAAGGAAAUUGAAUUCAUUUA | 16 |
| hsa-miR-1260 | MIMAT0005911 | AUCCCACCUCUGCCACCA | 17 |
| hsa-miR-1271 | MIMAT0005796 | CUUGGCACCUAGCAAGCACUCA | 18 |

TABLE 5

OncomiR that sustains the malignant phenotype of human salivary gland cancer cells

| ID | Accession No. | Sequence (5'→3') | Seq ID |
|---|---|---|---|
| hsa-miR-133a/b | MIMAT0000427 | UUUGGUCCCCUUCAACCAGCUG | 1 |
|  | MIMAT0000770 | UUUGGUCCCCUUCAACCAGCUA | 2 |
| hsa-miR-361-3p | MIMAT0004682 | UCCCCCAGGUGUGAUUCUGAUUU | 4 |

2. Confirmation of Proliferation Inhibition by Introducing Antisense Oligonucleotide Antisense oligonucleotides shown below to hsa-miR-133a/b, hsa-miR-346, and hsa-miR-361-3p were introduced to oral squamous cell cancer cells GFP-SAS under the conditions shown below, and influences to the cell proliferation were evaluated.

[Antisense Oligonucleotides Used]

As antisense oligonucleotides to hsa-miR-133a/b, hsa-miR-346, and hsa-miR-361-3p, knockdown probes having the sequences shown in Table 6 below (trade name: miRCURY LNA microRNA Inhibitor, manufactured by EXIQON) were used. It should be noted that as the negative control, a miRCURY Knockdown control probe (trade name, SEQ ID NO. 32, manufactured by EXIQON) was used. These oligonucleotides contained LNAs (trade name: Locked Nucleic Acid) (each oligonucleotide contained LNA of about 8 bases with respect to a DNA of about 20 bases).

[Introduction of miRNA Knockdown Probe and Cell Proliferation Evaluation]

The following were mixed and placed in each well of 96-well plastic plates: complete medium containing $2\times10^3$ human cancer cells of various types, 80 μl each; knockdown probe having the sequence shown in Table 3 below to miRNA, 2.5 pmol each; and Opti-MEM (manufactured by Invitrogen) containing 0.2 μl of RNAiMAX (manufactured by Invitrogen), 20 μl each. After cultivation for 80 hours, a fluorescence of GFP emitted by surviving cells in each well was observed by fluorescence microscope. The results obtained are shown in FIG. 1.

As shown in FIG. 1, antisense oligonucleotides to hsa-miR-133a/b, hsa-miR-346, and hsa-miR-361-3p in Table 6 below completely suppressed the proliferation of human oral squamous cell cancer GFP-SAS.

TABLE 6

Antisense Oligonucleotide to OncomiR

| miRNA ID | Sequence (5'→3') | Seq ID |
|---|---|---|
| hsa-miR-133a/b | AGCTGGTTGAAGGGGACCAA | 29 |
| hsa-miR-346 | GAGGCAGGCATGCGGGCAGAC | 30 |
| hsa-miR-361-3p | AATCAGAATCACACCTGGGGG | 31 |
| Control | GTGTAACACGTCTATACGCCCA | 32 |

3. Confirmation of Inhibition of Proliferation of Various Cancer Cells by Introducing Antisense Oligonucleotides Antisense oligonucleotides shown in Table 6 above to hsa-miR-133a/b, hsa-miR-346, and hsa-miR-361-3p were introduced to cancer cells of various types and influences to the cell proliferation were evaluated, under the conditions shown below.

[Antisense Oligonucleotides Used]

In addition to GFP stably expressing cell lines GFP-SAS and GFP-ACCM that were obtained by introducing green fluorescent protein (GFP) genes into human oral squamous cell cancer cell lines SAS and human salivary gland cancer cell lines ACCM and separating and establishing the same, the following were used: human oral squamous cell cancer cell lines B88; human pancreas cancer cell lines MIAPaCa-2; human biliary tract cancer cell lines HuCCT1; human lung squamous cell cancer cell lines EBC-1; human lung adenocarcinoma cell lines A549; and human prostate cancer cell lines LNCaP (androgen dependent) and PC-3 (androgen independent). For the cultivation of these cell lines, Dulbecco's modified Eagle medium (DMEM) or RPMI1640 medium (manufactured by Sigma-Aldrich) containing 10% fetal bovine serum (FBS, manufactured by Biosource International), 100 µg/ml streptomycin, 100 U/ml penicillin, and 0.25 mg/ml amphotericin B (manufactured by Invitrogen) was used as a proliferation culture solution. The culturing was carried out at 37° C. in an incubator filled with air containing carbon dioxide gas at a rate of 5%.

[Introduction of miRNA Knockdown Probe and Cell Proliferation Evaluation Method]

The following were mixed and placed in each well of 96-well plastic plates: complete medium containing $2 \times 10^3$ human cancer cells of various types, 80 µl each; knockdown probe having the sequence shown in Table 3 above to miRNA, 2.5 pmol each; and Opti-MEM (manufactured by Invitrogen) containing 0.2 µl of RNAiMAX (manufactured by Invitrogen), 20 µl each. After cultivation for 80 hours, the number of cells in each well was counted by using Cell Counting Kit-8 (manufactured by Dojindo). It should be noted that as the negative control, a miRCURY Knockdown control probe (trade name, SEQ ID NO. 32, manufactured by EXIQON) was used. The results are shown in FIG. 2.

Figure 2:
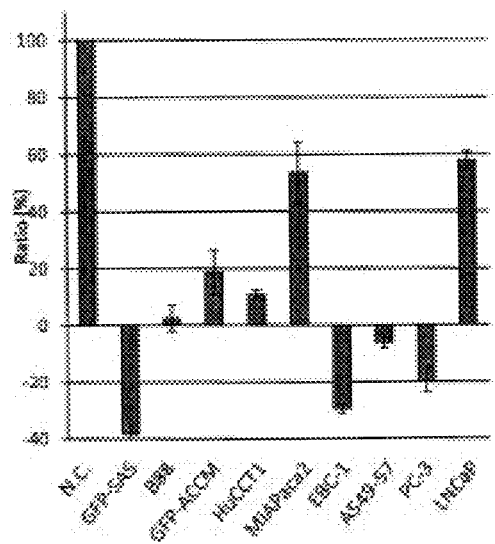
FIG. 2 is an exemplary graph showing influences of antisense oligonucleotides to microRNAs with respect to proliferation of various cancer cells.
Figure 2:
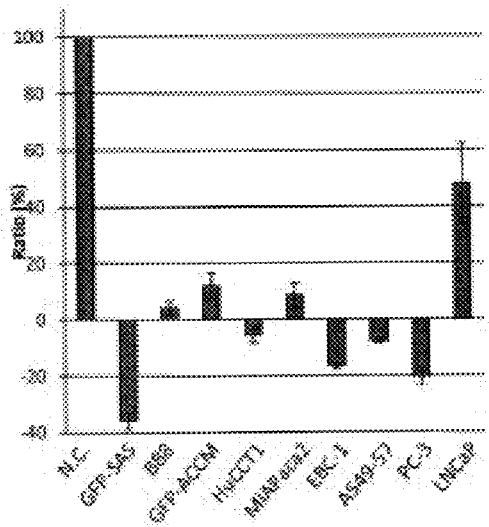
Figure 2:
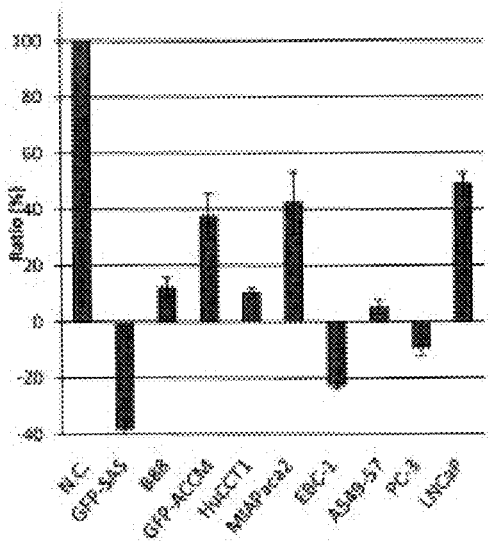

As shown in FIG. 2, the antisense oligonucleotides to hsa-miR-133a/b, hsa-miR-346, and hsa-miR-361-3p shown in Table 6 above exhibited the proliferation inhibition effect against cancer cells other than those of head/neck cancers.

Figure 3:
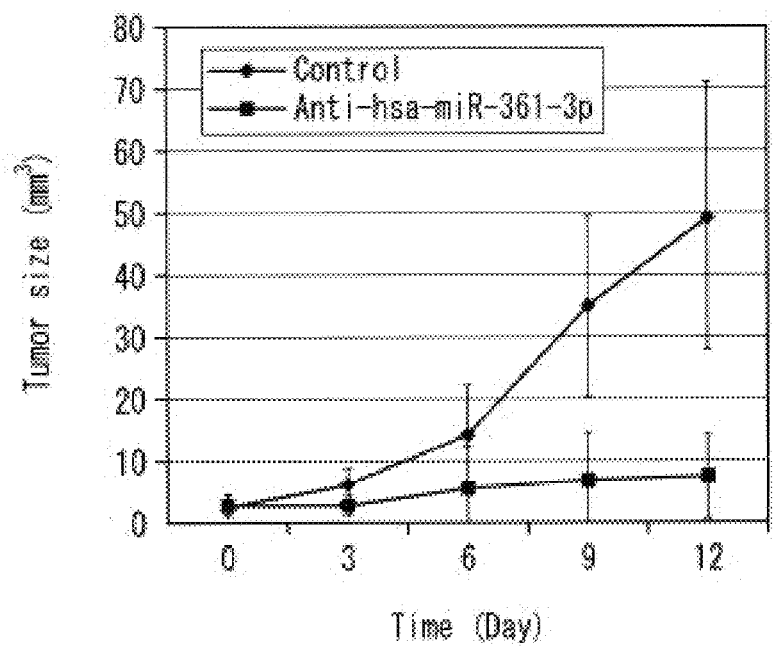
FIG. 3 is a graph showing exemplary cancer cell proliferation inhibition effects exerted by antisense oligonucleotides to microRNAs in vivo.
Figure 4:
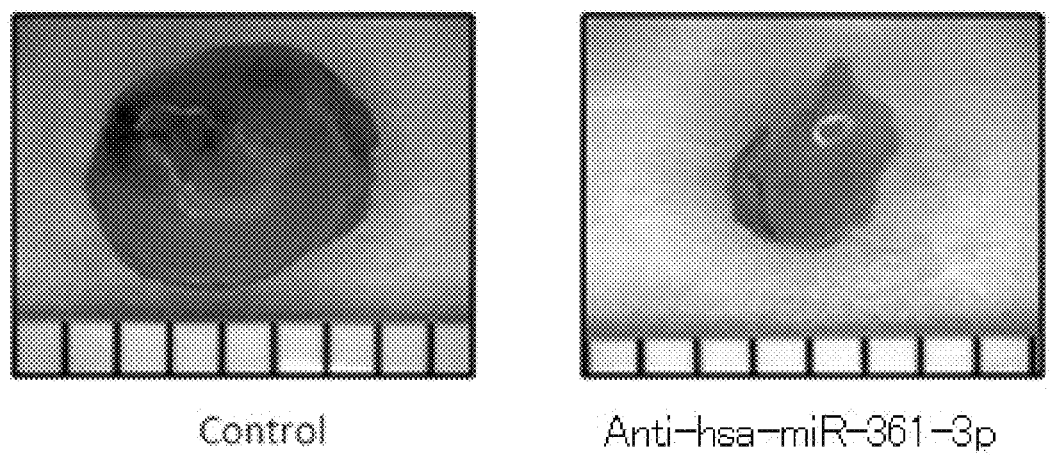
FIG. 4 is a photograph showing exemplary cancer cell proliferation inhibition effects exerted by antisense oligonucleotides to microRNAs in vivo.

4. Confirmation of In-Vivo Cancer Cell Proliferation Inhibition by Antisense Oligonucleotide to hsa-miR-361-3p The antisense oligonucleotide to hsa-miR-361-3p and a negative control were administered to tumor model mice under the conditions shown below, and the growth (size) of tumors with time was observed. The results are shown in FIGS. 3 and 4. FIG. 3 is a graph of sizes of tumors determined under the following conditions 3, 6, 9, and 12 days after the administration of the antisense oligonucleotide and the control, and FIG. 4 shows photographs of the tumors 12 days after the administration.

[Tumor Model Mouse, Antisense Oligonucleotide Administration Method and Observation Method]

A tumor model mouse was obtained by subcutaneously transplanting $1 \times 10^6$ GFP-SAS cells to a 6-week-old male Balb/C nude mouse at the back. A tumor was recognized to be formed 12 days after the transplantation, and an LNA/DNA antisense oligonucleotide to hsa-miR-361-3p and a control LNA/DNA oligonucleotide (both were phosphorothioate oligonucleotides having base sequences shown in Table 6 above; each oligonucleotide contained LNA of about 8 bases with respect to a DNA of about 20 bases), 8 nmol each, were systemically administered via tail vein. Further 7 days after, the same were systemically administered in the same manner. Volumes of the tumors were determined 3, 6, 9, and 12 days after the first administration by using a calculation formula of [tumor volume=major diameter length×minor diameter length×height×0.5236], whereby antitumor activity of the anti-hsa-miR-361-3p antisense oligonucleotide was evaluated.

As shown in FIGS. 3 and 4, the antisense oligonucleotide to hsa-miR-361-3p exhibited the cancer cell proliferation inhibition effect in vivo as well.

INDUSTRIAL APPLICABILITY

The present invention is useful in the pharmaceutical development relating to cancers, the field of medical treatments for cancer, the field of cancer research, and the like.

SEQUENCE LISTING FREE TEXT

SEQ ID NOS. 1 to 4: Sequences of microRNAs registered in miRBase (hsa-miR-133a/b MIMAT0000427/MIMAT0000770, hsa-miR-346 MIMAT0000773, hsa-miR-361-3p MIMAT0004682).

SEQ ID NOS. 5 to 8: Sequences complementary to SEQ ID NOS. 1 to 4.

SEQ ID NOS. 9 to 18: Sequences of microRNAs registered in miRBase (hsa-miR-92a MIMAT0000092, hsa-miR-139-5p MIMAT0000250, hsa-miR-197 MIMAT0000227, hsa-miR-328 MIMAT0000752, hsa-miR-605 MIMAT0003273, hsa-miR-766 MIMAT0003888, hsa-miR-1228 MIMAT0005583, hsa-miR-1252 MIMAT0005944, hsa-miR-1260 MIMAT0005911, hsa-miR-1271 MIMAT0005796)

SEQ ID NOS. 19 to 28: Sequences complementary to SEQ ID NOS. 9 to 18.

SEQ ID NO. 29: anti-hsa-miR-133a/b antisense oligonucleotide.

SEQ ID NO. 30: anti-hsa-miR-346 antisense oligonucleotide.

SEQ ID NO. 31: anti-hsa-miR-361-3p antisense oligonucleotide.

SEQ ID NO. 32: negative control.

The invention claimed is:

1. A method of suppressing growth of human cancer cells, the method comprising:
bringing a composition comprising an effective amount of an antisense oligonucleotide to a microRNA into contact with the cancer cells,
wherein the cancer is selected from the group consisting of head/neck cancer and biliary tract cancer, and
the microRNA is selected from the group consisting of hsa-miR-133a, hsa-miR-133b, and hsa-miR-361-3p.

2. A method of treating a human cancer in a subject, the method comprising:
administering a composition comprising an effective amount of an antisense oligonucleotide to a microRNA to the subject,
wherein the cancer is selected from the group consisting of head/neck cancer and biliary tract cancer, and
the microRNA is selected from the group consisting of hsa-miR-133a, hsa-miR-133b, and hsa-miR-361-3p.

3. The method according to claim 1, wherein the antisense oligonucleotide comprises the base sequence of SEQ ID NO: 29, and the antisense oligonucleotide to hsa-miR-361-3p comprises the base sequence of SEQ ID NO: 31.

4. The method according to claim 2, wherein the antisense oligonucleotide comprises the base sequence of SEQ ID NO: 29, and the antisense oligonucleotide to hsa-miR-361-3p comprises the base sequence of SEQ ID NO: 31.

5. The method according to claim 1, wherein the antisense oligonucleotide consists of the base sequence of SEQ ID NO: 29, and the antisense oligonucleotide to hsa-miR-361-3p consists of the base sequence of SEQ ID NO: 31.

6. The method according to claim 2, wherein the antisense oligonucleotide consists of the base sequence of SEQ ID NO: 29, and the antisense oligonucleotide to hsa-miR-361-3p consists of the base sequence of SEQ ID NO: 31.

7. The method according to claim 1, wherein the cancer is head/neck cancer.

8. The method according to claim 2, wherein the cancer is head/neck cancer.

9. The method according to claim 7, wherein the head/neck cancer is oral squamous cell cancer.

10. The method according to claim 8, wherein the head/neck cancer is oral squamous cell cancer.

11. A method of treating a human cancer in a subject, the method comprising:
administering a composition comprising an effective amount of an antisense oligonucleotide to a microRNA to the subject,
wherein the cancer is selected from the group consisting of head/neck cancer and biliary tract cancer, and
the antisense oligonucleotide to the microRNA is an antisense oligonucleotide to hsa-miR-361-3p or an oligonucleotide consisting of a base sequence of SEQ ID No: 29.

12. The method according to claim 11, wherein the antisense oligonucleotide to the microRNA comprises the base sequence of SEQ ID NO: 31.

13. The method according to claim 11, wherein the antisense oligonucleotide to the microRNA consists of the base sequence of SEQ ID NO: 31.

* * * * *

SEQUENCE LISTING

```
<160> NUMBER OF SEQ ID NOS: 32

<210> SEQ ID NO 1
<211> LENGTH: 22
<212> TYPE: RNA
<213> ORGANISM: Homo sapiens
```

-continued

```
<400> SEQUENCE: 1
uuuggucccc uucaaccagc ug                                        22

<210> SEQ ID NO 2
<211> LENGTH: 22
<212> TYPE: RNA
<213> ORGANISM: Homo sapiens

<400> SEQUENCE: 2
uuuggucccc uucaaccagc ua                                        22

<210> SEQ ID NO 3
<211> LENGTH: 23
<212> TYPE: RNA
<213> ORGANISM: Homo sapiens

<400> SEQUENCE: 3
ugucugcccg caugccugcc ucu                                       23

<210> SEQ ID NO 4
<211> LENGTH: 23
<212> TYPE: RNA
<213> ORGANISM: Homo sapiens

<400> SEQUENCE: 4 uccccaggu gugauucuga uuu                                        23

<210> SEQ ID NO 5
<211> LENGTH: 22
<212> TYPE: DNA
<213> ORGANISM: Artificial Sequence
<220> FEATURE:
<223> OTHER INFORMATION: Complement sequence of hsa-miR-133a

<400> SEQUENCE: 5
cagctggttg aagggggacca aa                                       22

<210> SEQ ID NO 6
<211> LENGTH: 22
<212> TYPE: DNA
<213> ORGANISM: Artificial Sequence
<220> FEATURE:
<223> OTHER INFORMATION: Complement sequence of hsa-miR-133b

<400> SEQUENCE: 6
tagctggttg aagggggacca aa                                       22

<210> SEQ ID NO 7
<211> LENGTH: 23
<212> TYPE: DNA
<213> ORGANISM: Artificial Sequence
<220> FEATURE:
<223> OTHER INFORMATION: Complement sequence of hsa-miR-346

<400> SEQUENCE: 7
agaggcaggc atgcgggcag aca                                       23

<210> SEQ ID NO 8
<211> LENGTH: 23
<212> TYPE: DNA
<213> ORGANISM: Artificial Sequence
<220> FEATURE:
<223> OTHER INFORMATION: Complement sequence of hsa-miR-361-3p

<400> SEQUENCE: 8
```

```
aaatcagaat cacacctggg gga                                              23

<210> SEQ ID NO 9
<211> LENGTH: 22
<212> TYPE: RNA
<213> ORGANISM: Homo sapiens

<400> SEQUENCE: 9
uauugcacuu gucccggccu gu                                               22

<210> SEQ ID NO 10
<211> LENGTH: 22
<212> TYPE: RNA
<213> ORGANISM: Homo sapiens

<400> SEQUENCE: 10
ucuacagugc acgugucucc ag                                               22

<210> SEQ ID NO 11
<211> LENGTH: 22
<212> TYPE: RNA
<213> ORGANISM: Homo sapiens

<400> SEQUENCE: 11
uucaccaccu ucuccaccca gc                                               22

<210> SEQ ID NO 12
<211> LENGTH: 22
<212> TYPE: RNA
<213> ORGANISM: Homo sapiens

<400> SEQUENCE: 12
cuggcccucu cugcccuucc gu                                               22

<210> SEQ ID NO 13
<211> LENGTH: 23
<212> TYPE: RNA
<213> ORGANISM: Homo sapiens

<400> SEQUENCE: 13
uaaaucccau ggugccuucu ccu                                              23

<210> SEQ ID NO 14
<211> LENGTH: 22
<212> TYPE: RNA
<213> ORGANISM: Homo sapiens

<400> SEQUENCE: 14
acuccagccc cacagccuca gc                                               22

<210> SEQ ID NO 15
<211> LENGTH: 20
<212> TYPE: RNA
<213> ORGANISM: Homo sapiens

<400> SEQUENCE: 15
ucacaccugc cucgccccc                                                   20

<210> SEQ ID NO 16
<211> LENGTH: 22
<212> TYPE: RNA
<213> ORGANISM: Homo sapiens
```

<400> SEQUENCE: 16
agaaggaaau ugaauucauu ua                                    22

<210> SEQ ID NO 17
<211> LENGTH: 18
<212> TYPE: RNA
<213> ORGANISM: Homo sapiens

<400> SEQUENCE: 17
aucccaccuc ugccacca                                         18

<210> SEQ ID NO 18
<211> LENGTH: 22
<212> TYPE: RNA
<213> ORGANISM: Homo sapiens

<400> SEQUENCE: 18
cuuggcaccu agcaagcacu ca                                    22

<210> SEQ ID NO 19
<211> LENGTH: 22
<212> TYPE: DNA
<213> ORGANISM: Artificial Sequence
<220> FEATURE:
<223> OTHER INFORMATION: Coplement sequence of hsa-miR-92a

<400> SEQUENCE: 19
acaggccggg acaagtgcaa ta                                    22

<210> SEQ ID NO 20
<211> LENGTH: 22
<212> TYPE: DNA
<213> ORGANISM: Artificial Sequence
<220> FEATURE:
<223> OTHER INFORMATION: Complement sequence of hsa-miR-139-5p

<400> SEQUENCE: 20
ctggagacac gtgcactgta ga                                    22

<210> SEQ ID NO 21
<211> LENGTH: 22
<212> TYPE: DNA
<213> ORGANISM: Artificial Sequence
<220> FEATURE:
<223> OTHER INFORMATION: Complement sequence of hsa-miR-197

<400> SEQUENCE: 21
gctgggtgga gaaggtggtg aa                                    22

<210> SEQ ID NO 22
<211> LENGTH: 22
<212> TYPE: DNA
<213> ORGANISM: Artificial Sequence
<220> FEATURE:
<223> OTHER INFORMATION: Complement sequence of hsa-miR-328

<400> SEQUENCE: 22
acggaagggc agagagggcc ag                                    22

<210> SEQ ID NO 23
<211> LENGTH: 23
<212> TYPE: DNA
<213> ORGANISM: Artificial Sequence
<220> FEATURE:
<223> OTHER INFORMATION: Complement sequecne of hsa-miR-605

```
<400> SEQUENCE: 23
aggagaaggc accatgggat tta                                             23

<210> SEQ ID NO 24
<211> LENGTH: 22
<212> TYPE: DNA
<213> ORGANISM: Artificial Sequence
<220> FEATURE:
<223> OTHER INFORMATION: Complement sequence of has-miR-766

<400> SEQUENCE: 24
gctgaggctg tggggctgga gt                                              22

<210> SEQ ID NO 25
<211> LENGTH: 20
<212> TYPE: DNA
<213> ORGANISM: Artificial Sequence
<220> FEATURE:
<223> OTHER INFORMATION: Complement sequence of hsa-miR-1228

<400> SEQUENCE: 25 gggggggcgag gcaggtgtga                                                20

<210> SEQ ID NO 26
<211> LENGTH: 22
<212> TYPE: DNA
<213> ORGANISM: Artificial Sequence
<220> FEATURE:
<223> OTHER INFORMATION: Complement sequence of hsa-miR-1252

<400> SEQUENCE: 26
taaatgaatt caatttcctt ct                                              22

<210> SEQ ID NO 27
<211> LENGTH: 18
<212> TYPE: DNA
<213> ORGANISM: Artificial Sequence
<220> FEATURE:
<223> OTHER INFORMATION: Complement sequece of hsa-miR-1260

<400> SEQUENCE: 27
tggtggcaga ggtgggat                                                   18

<210> SEQ ID NO 28
<211> LENGTH: 22
<212> TYPE: DNA
<213> ORGANISM: Artificial Sequence
<220> FEATURE:
<223> OTHER INFORMATION: Complement sequece of hsa-miR-1271

<400> SEQUENCE: 28
tgagtgcttg ctaggtgcca ag                                              22

<210> SEQ ID NO 29
<211> LENGTH: 20
<212> TYPE: DNA
<213> ORGANISM: Artificial Sequence
<220> FEATURE:
<223> OTHER INFORMATION: anti-hsa-miR-133a/b oligonucleotide

<400> SEQUENCE: 29
agctggttga agggaccaa                                                  20

<210> SEQ ID NO 30
```

```
<211> LENGTH: 21
<212> TYPE: DNA
<213> ORGANISM: Artificial Sequence
<220> FEATURE:
<223> OTHER INFORMATION: anti-hsa-miR-346 oligonucleotide

<400> SEQUENCE: 30
gaggcaggca tgcgggcaga c                                            21

<210> SEQ ID NO 31
<211> LENGTH: 21
<212> TYPE: DNA
<213> ORGANISM: Artificial Sequence
<220> FEATURE:
<223> OTHER INFORMATION: anti-hsa-miR-361-3p oligonucleotide

<400> SEQUENCE: 31
aatcagaatc acacctgggg g                                            21

<210> SEQ ID NO 32
<211> LENGTH: 22
<212> TYPE: DNA
<213> ORGANISM: Artificial Sequence
<220> FEATURE:
<223> OTHER INFORMATION: Knockdown control probe

<400> SEQUENCE: 32
gtgtaacacg tctatacgcc ca                                           22
```